(12) United States Patent
Brown

(10) Patent No.: US 7,724,147 B2
(45) Date of Patent: May 25, 2010

(54) MEDICAL NOTIFICATION APPARATUS AND METHOD

(75) Inventor: Houston Brown, Poway, CA (US)

(73) Assignee: Cardinal Health 303, Inc., San Diego, CA (US)

(*) Notice: Subject to any disclaimer, the term of this patent is extended or adjusted under 35 U.S.C. 154(b) by 0 days.

(21) Appl. No.: 11/485,932

(22) Filed: Jul. 13, 2006

(65) Prior Publication Data
US 2008/0018435 A1   Jan. 24, 2008

(51) Int. Cl.
*G08B 23/00* (2006.01)
(52) U.S. Cl. .............. 340/573.1; 340/531; 340/286.07; 340/539.1; 600/300
(58) Field of Classification Search ............ 340/573.1, 340/531, 286.07, 539.1; 600/300, 484, 507, 600/502, 528
See application file for complete search history.

(56) References Cited

U.S. PATENT DOCUMENTS

| | | |
|---|---|---|
| 3,582,671 A | 6/1971 | Ott |
| 3,593,703 A | 7/1971 | Gunn |
| 3,668,682 A | 6/1972 | Barbee et al. |
| 3,998,209 A | 12/1976 | Macvaugh |
| 4,001,805 A | 1/1977 | Golbe |
| 4,214,229 A | 7/1980 | Warner |
| 4,215,241 A | 7/1980 | Pinkney, Jr. |
| 4,450,436 A | 5/1984 | Massa |
| 4,473,821 A * | 9/1984 | Yang et al. ............. 340/539.11 |
| 4,520,349 A | 5/1985 | Varano |
| 4,522,213 A * | 6/1985 | Wallroth et al. ............. 600/529 |
| 4,540,984 A | 9/1985 | Waldman |
| 4,619,270 A | 10/1986 | Margolis et al. |
| 4,785,474 A | 11/1988 | Bernstein et al. |
| 4,792,798 A | 12/1988 | Wilowski |
| 4,876,721 A | 10/1989 | Kerr et al. |
| 4,882,566 A | 11/1989 | Koerber, Sr. et al. |
| 4,935,952 A | 6/1990 | Dutra |
| 4,947,152 A | 8/1990 | Hodges |
| 5,022,402 A * | 6/1991 | Schieberl et al. ............. 600/484 |
| 5,432,495 A * | 7/1995 | Tompkins ............. 340/429 |
| 5,435,317 A | 7/1995 | McMahon et al. |

(Continued)

FOREIGN PATENT DOCUMENTS

EP          1623666          2/2006

OTHER PUBLICATIONS

International Search Report No. WO/2008/008916 A3, dated Jan. 17, 2008.

*Primary Examiner*—Anh V La
(74) *Attorney, Agent, or Firm*—McDermott Will & Emery LLP

(57) ABSTRACT

A medical notification apparatus and method for use with a preexisting healthcare facility nurse call system are disclosed. The apparatus sends a message signal to the healthcare facility call system when the apparatus receives and identifies an acoustic signal indicative of a medical device alarm or other parameter. The apparatus comprises an acoustic sensor, a signal processing unit, and an interface unit. A band pass filter, timing gate, and a processor are configured in one embodiment to process the received acoustic signal to identify an acoustic alarm. A memory device may be used to store a set of identification criteria for identifying a variety of acoustic alarms, and to store a set of message signals. The sent message signal is selected from among the stored set of message signals.

20 Claims, 7 Drawing Sheets

U.S. PATENT DOCUMENTS

| | | | |
|---|---|---|---|
| 5,497,787 A * | 3/1996 | Nemesdy et al. | 600/587 |
| 5,592,153 A | 1/1997 | Welling et al. | |
| 5,684,460 A | 11/1997 | Scanlon | |
| 5,708,970 A | 1/1998 | Newman et al. | |
| 5,838,223 A | 11/1998 | Gallant et al. | |
| 5,853,005 A | 12/1998 | Scanlon | |
| 6,048,310 A | 4/2000 | Yasushi et al. | |
| 6,215,404 B1 | 4/2001 | Morales | |
| 6,445,299 B1 | 9/2002 | Rojas, Jr. | |
| 6,496,115 B2 | 12/2002 | Arakawa | |
| 6,544,200 B1 | 4/2003 | Smith et al. | |
| 6,775,577 B2 * | 8/2004 | Crnkovich et al. | 700/11 |
| 7,126,467 B2 * | 10/2006 | Albert et al. | 340/521 |
| 7,148,797 B2 | 12/2006 | Albert | |
| 2002/0070866 A1 | 6/2002 | Newham | |
| 2002/0101349 A1 | 8/2002 | Rojas, Jr. | |
| 2002/0135485 A1 | 9/2002 | Arakawa | |
| 2002/0186123 A1 | 12/2002 | Kivisto et al. | |
| 2006/0077063 A1 * | 4/2006 | Cheng et al. | 340/573.1 |

* cited by examiner

MEDICAL NOTIFICATION APPARATUS AND METHOD

The invention relates generally to a medical notification apparatus and method and, more particularly, to automatically providing a notification to a preexisting healthcare facility call system upon detection of the existence of a particular medical event signal.

BACKGROUND OF THE INVENTION

In a patient healthcare environment, such as a hospital room, certain patient monitoring devices and treatment devices provide acoustic signals indicative of status. Some of those signals can relate to a patient condition or can relate to a medical device condition for which a clinician should be called or alerted as soon as possible. Other acoustic signals are of lesser importance and should not be the basis for interrupting a clinician in the performance of other tasks. Additionally, there may be other acoustic signals generated in a patient hospital room that are completely unrelated to patient care and for which no clinician attention should be given. For example, patient visitors may bring mobile telephones that emit unusual acoustic sounds or signals, or visitors may have other electronic devices, such as portable computers, that emit acoustic signals, none of which should form the basis for alerting the healthcare staff. Televisions, radios, and intercoms in patient rooms may also emit sounds which should be distinguished from acoustic signals from medical devices.

An example of a medical device acoustic signal is that given by an infusion pump when the tubing of the medication administration set becomes occluded downstream of the pump so that the infusion of medical fluid to the patient is interrupted. Most infusion pumps will provide an acoustic signal that will communicate to a clinician that there is a problem with the infusion. These acoustic signals can be quite loud and are meant to attract attention. However, there are times when the person charged with supervising the medical device is not close enough to the medical device to hear the acoustic alarm signal. Making the acoustic alarm signal louder so that it may be heard from a greater distance is undesirable since it would disturb patients in other rooms.

In prior attempts to solve this problem, some medical devices were configured to communicate directly, via wired or wireless means, to a preexisting healthcare facility communications network or "nurse call" system. However, wires may be cumbersome and present a hazard, especially when the medical device is located at a significant distance from a nurse call communications port. Wires are also inconvenient because they must disconnected when the medical device is moved out of a patient's room. Furthermore, wires are undesirable because they may inadvertently remain disconnected when the medical device is returned to the room. Many facilities do not include a wireless nurse call system and when they do, in some cases the wireless communications protocol may differ from that of the medical device thereby preventing an operable connection. Whether wired or wireless means are used, a medical device designed to operate with a particular nurse call system of a healthcare facility must incorporate communications hardware and software which make the device more expensive. A healthcare institution may be unwilling to replace older medical devices with newer, more expensive devices that incorporate such necessary communications hardware and software. The increased expense may be prohibitive especially when multiplied by tens or hundreds of medical devices in a healthcare facility.

As shown in FIG. 1, typical nurse call systems in healthcare facilities often include a panel 100 on the wall of a patient's room 102. The panel is often located near the patient's bed and typically comprises a jack or connector 104 of some type that accepts a plug 106 with a long cable 108 terminating in a nurse call button or switch 110 at the patient's bedside. The patient 112 manually actuates the nurse call button whenever the patient needs assistance from a clinician 114 who may be located at a remote clinician station 116. The patient may also actuate the nurse call button whenever a medical device 118 in the patient's room generates an acoustic alarm to alert the clinician of the alarm.

When the nurse call signal is activated by the patient, the clinician can determine from which room the signal originated because the rooms are individually displayed at, typically, the clinician workstation 117 in the clinician station. The clinician workstation 117 can also have an acoustic alarm in combination with a visual indicator that alert a clinician that a nurse call has been initiated. More sophisticated workstations are capable of being programmed to contact a nurse-in-charge who has a portable communication device. Portable communication devices include, without limitation, pagers, personal digital assistants ("PDAs"), and mobile telephones. Some healthcare facilities include an Ethernet network system to which the nurse call system is connected. Such nurse call systems can send text or other coded messages to the clinician.

As previously mentioned, clinicians are not always present in the same room as a patient and the medical devices connected to the patient. In addition, a medical device emitting an acoustic alarm that is not heard and responded to by a clinician for any period of time may cause anxiety in patients. Furthermore, it may be difficult for a clinician to immediately pinpoint which room or patient has a medical device that is emitting an alarm in situations where there are many patients connected to numerous medical devices. Another consideration is that there are times when the patient is asleep, unconscious, or is physically unable to actuate the nurse call button.

Hence a need has been recognized by those skilled in the art for an automatic apparatus and method for notifying a clinician of an acoustic alarm generated by a medical device. There is also a need for a simple and inexpensive means of automatically sending a signal or message to an existing nurse call system in response to medical device acoustic alarms. To lessen the chances of a false alarm and to allow customization to suit the needs of a clinician, there is a further need for such an apparatus and method to distinguish between acoustic signals of no importance and those of importance to the clinician. The present invention satisfies these and other needs.

SUMMARY OF THE INVENTION

Briefly and in general terms, the present invention is directed to a medical notification apparatus and method for transmitting a message to a preexisting healthcare facility call system in response to acoustic alarms produced by medical devices. In a detailed aspect of the invention, a medical notification apparatus comprises an acoustic sensor configured to generate a sensor signal in response to an acoustic alarm indicative of a medical device parameter; a signal processing unit in communication with the acoustic sensor and configured to generate an identification signal when the sensor signal from the acoustic sensor satisfies an identification criterion; and an interface unit in communication with the signal processing unit and configured to send a message signal to a healthcare facility call system in response to the identification signal from the signal processing unit.

In more detailed aspects of the invention, the signal processing unit comprises a signal conditioner having an automatic level adjuster, the signal conditioner adapted to smooth the sensor signal. The signal processing unit comprises a band pass filter. The signal processing unit comprises a timing gate. The signal processing unit comprises an active filter. The signal processing unit comprises a processor adapted to execute a fast Fourier transform routine to analyze the sensor signal.

In further aspects of the invention, the identification criterion comprises a frequency band. The identification criterion comprises a pulse pattern.

In still further aspects, the interface unit comprises a switch configured to produce a contact closure in response to the identification signal from the signal processing unit. The interface unit comprises a radio frequency transmitter configured to transmit a radio frequency signal to the healthcare facility call system in response to the identification signal from the signal processing unit. The interface unit comprises a radio frequency transmitter and is configured to transmit a radio frequency signal to a portable communications device in response to the identification from the signal processing unit. The interface unit comprises an Ethernet driver and is configured to transmit an electronic message to the healthcare facility call system in response to the identification signal from the signal processing unit.

In more detailed aspects of the invention, the medical notification apparatus comprises a memory unit associated with the signal processing unit, the memory unit storing the identification criterion.

In further aspects, the medical notification apparatus comprises a memory unit associated with the interface unit, the memory unit storing a set of message signals, each one of the set of message signals associated with a different medical device alarm; and wherein the message signal sent to the healthcare facility call system is selected from among the stored set of message signals.

In another aspect of the invention, a medical notification apparatus for use with a healthcare facility call system, the medical notification apparatus comprises an acoustic sensor configured to generate a sensor signal representative of an acoustic alarm received by the acoustic sensor, the acoustic alarm associated with a medical device parameter; a signal processing unit connected to the acoustic sensor and configured to store an identification criterion and to determine whether the sensor signal from the acoustic sensor satisfies the stored identification criterion; and an interface unit connected to the signal processing unit and configured to send a message signal to the healthcare facility call system when the sensor signal from the signal processing unit satisfies the stored identification criterion.

In yet another aspect of the invention, a method of providing medical notification, the method comprises sensing an acoustic alarm indicative of a medical device parameter; and sending a message signal from a medical notification apparatus to a healthcare facility call system in response to the medical notification apparatus identifying the acoustic alarm.

In detailed aspects, sending the message from the medical notification apparatus comprises determining whether the acoustic alarm satisfies an identification criterion, and generating the message signal when the acoustic alarm satisfies the identification criterion.

In other detailed aspects, sending the message from the medical notification apparatus comprises determining whether the acoustic alarm satisfies an identification criterion from among a set of identification criteria, and generating the message signal from among a set of message signals when the acoustic alarm satisfies the identification criterion, each one of the set of message signals associated with one of the set of identification criteria.

In yet a further detailed aspect, the method further comprises wirelessly transmitting a signal to a portable communications device in response to the acoustic alarm satisfying an identification criterion.

The features and advantages of the invention will be more readily understood from the following detailed description which should be read in conjunction with the accompanying drawings.

DETAILED DESCRIPTION OF PREFERRED EMBODIMENTS

Figure 1:
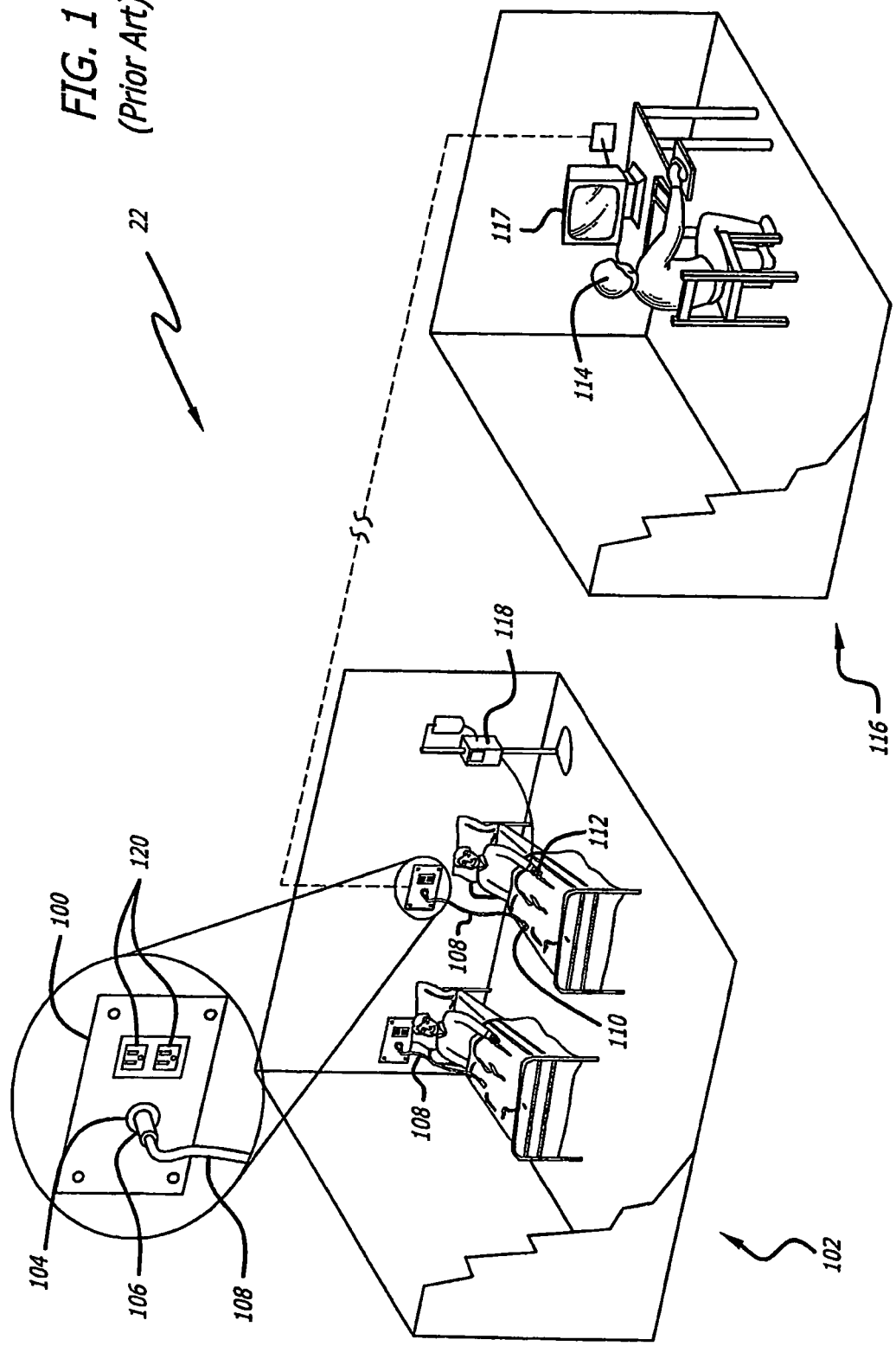
FIG. 1 provides a perspective view of a typical healthcare facility call system showing a nurse call panel mounted near a patient's bed, a nurse call button and cable connected with the nurse call panel with the button being located within reach of the patient, an alarming infusion pump adjacent the patient, and a clinician station to which the nurse call system is connected that informs the clinician at the station that a patient is pressing a nurse call button and desires assistance.

Referring now in more detail to the exemplary drawings for purposes of illustrating embodiments of the invention, wherein like reference numerals designate corresponding or like elements among the several views, there is shown in FIG. 1 a perspective view of a typical nurse call system presently existing in many healthcare facilities. The nurse call system, referred to more generally as a healthcare facility call system 22, includes a nurse call panel 100 located in this embodiment on a wall of a patient's room 102 having a communications port or jack 104 to which is connected a cooperatively shaped plug 106 on a cable 108 connected to a hand-held nurse call button 110. The nurse call button is manually actuated by a patient 112 in order to call a clinician 114 who may be located at a clinician station 116 located outside of the patient's room. Actuation of the nurse call button results in an alarm indication at the clinician workstation 117. The patient may call the clinician when a medical device 118, such as an infusion pump, located in the patient's room emits an acoustic alarm or when the patient desires assistance. In some cases, AC power outlets or sockets 120 are located on the nurse call panel for convenience in providing power to medical devices, lights, and other electrical appliances in the vicinity of the patient.

Figure 2:
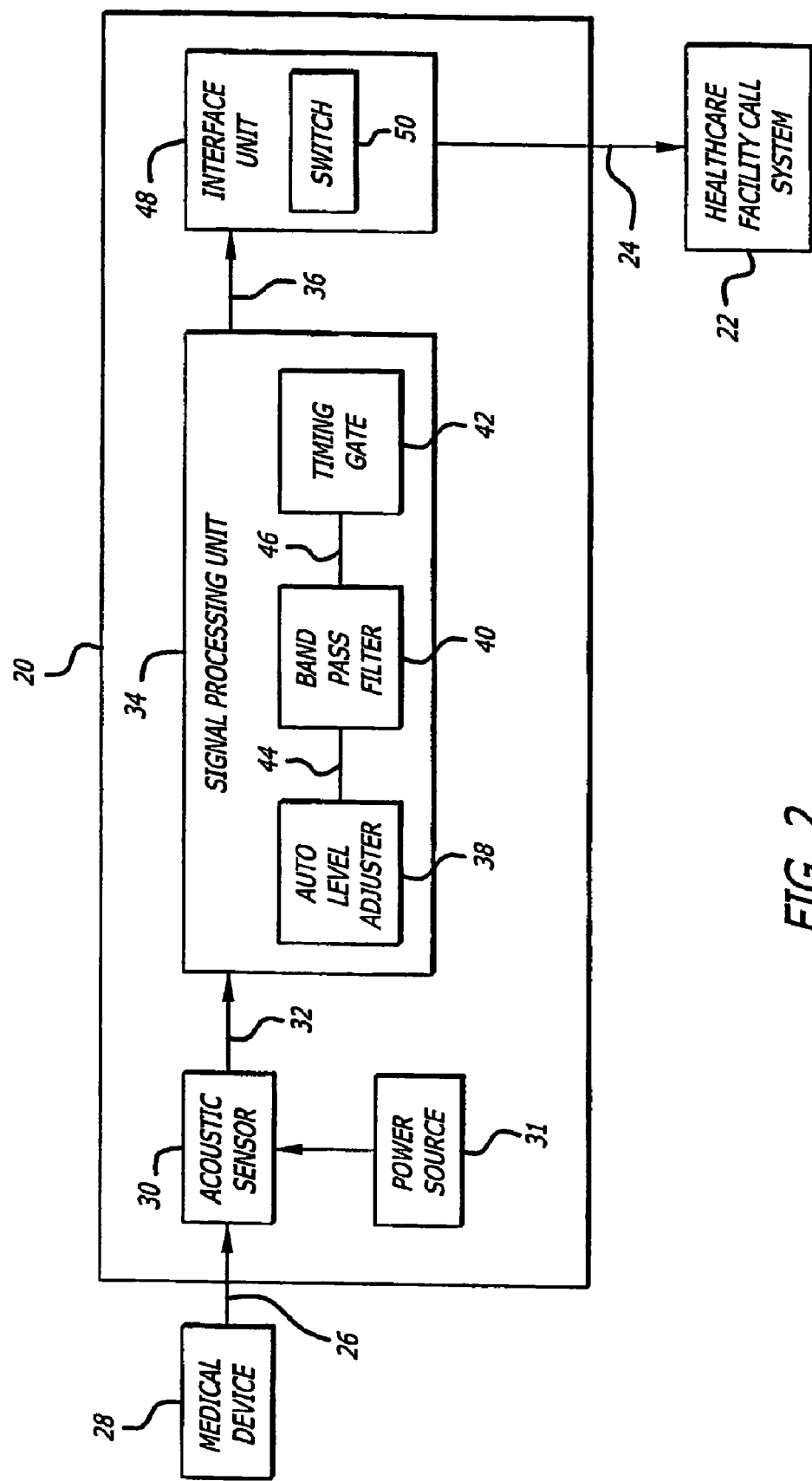
FIG. 2 is a block diagram of a medical notification apparatus in accordance with an embodiment of the present invention showing an acoustic sensor for generating a sensor signal in response to an acoustic alarm from a medical device, a signal processing unit comprising an automatic level adjuster, a band pass filter, and a timing gate for generating an identification signal, and an interface unit comprising a switch for sending a message signal to a healthcare facility call system in response to the identification signal.

Referring now to FIG. 2, there is shown a block diagram of a medical notification apparatus 20 in communication with a preexisting healthcare facility call system 22, such as a nurse call system in a hospital shown in FIG. 1. As discussed in further detail below, the medical notification apparatus 20 is adapted to send, via wired or wireless means, a message signal 24 to the healthcare facility call system in response to an identified acoustic alarm 26 from a medical device 28. As used herein, "medical device" refers to a device used to provide medical care to a patient, including but not limited to passive devices, such as pulse oximeters and other patient monitors, and active devices, such as ventilators, infusion pumps, and other medication delivery devices. Typically, the acoustic alarm is generated automatically, that is without active input from a patient or other person, by the medical device as an indication of a parameter of the medical device. The parameter of the medical device may relate to patient condition, the operational status of the medical device, or other variable condition. For example, a pulse oximeter may produce an acoustic alarm to indicate that a parameter representative of the patient's blood oxygen saturation level is at a certain level or when another parameter representative of the patient's pulse rate is at a certain level. Advantageously, because notification is sent to the healthcare facility call system, the person being notified may be located remotely and need not hear the acoustic alarm to be informed of a parameter of the medical device.

With continued reference to FIG. 2, the medical notification apparatus 20 comprises an acoustic sensor 30, such as a microphone, that produces a signal in response to sound. Preferably, the acoustic sensor generates an electrical sensor signal 32 representative of the sound of the acoustic alarm signal 26. The acoustic sensor and other elements of the medical notification apparatus obtain power from a power source 31 coupled to a preexisting AC power outlet (not shown) on the wall of the healthcare facility. The power source may also be coupled to a battery (not shown), including but not limited to standard D size load cells, that is part of the medical notification apparatus to allow operation of the medical notification apparatus in cases where there is no nearby AC power outlet or in the event of a power failure in the healthcare facility.

The medical notification apparatus 20 further comprises a signal processing unit 34 in communication with the acoustic sensor 30. The signal processing unit is configured to generate an identification signal 36 when the sensor signal 32 from the acoustic sensor satisfies a predetermined identification criterion. Preferably, the signal processing unit comprises a signal conditioner having an automatic level adjuster 38 for "smoothing" or modifying the amplitude or other characteristic of the sensor signal 32 to produce a conditioned sensor signal 44. Smoothing may be used to reduce the effects of background noise. The degree or level of modification is a matter of choice and may depend in part on the output characteristics of the acoustic sensor and the manner of signal processing to be performed.

The identification criterion, a predetermined frequency band and a pulse rate in this case, are determined with the selection of the characteristics of the band pass filter 40 and the timing gate 42. The characteristics of the band pass filter and the timing gate are carefully selected so that an identification signal is produced in response to only the acoustic alarms for which a notification through the healthcare facility call system 22 is desired. For example, the characteristics of the band pass filter and the timing gate may be selected so that audible tones from a television and arising from normal operation of a medical device do not result in a notification through the healthcare facility call system.

In the illustrated embodiment, the manner of signal processing involves a band pass filter 40 and a timing gate 42, both within the signal processing unit 34. The band pass filter is adapted to process the conditioned sensor signal 44 to allow only a predetermined frequency band to pass. If the conditioned sensor signal 44 comprises frequencies within the predetermined frequency band, a filtered sensor signal 46 is produced. When the acoustic alarm 26 has a pulsed sound, the timing gate is used to authenticate the acoustic alarm as matching a predetermined pulse rate or pattern. The signal processing unit generates the identification signal 36 when the acoustic alarm has a frequency within the predetermined frequency band and matches a predetermined pulse rate or pattern. In this case, the identification signal 36 may simply be the signal that passes through the timing gate 42.

Still referring to FIG. 2, the medical notification apparatus 20 further comprises an interface unit 48 in communication with the signal processing unit 34. The interface unit is configured to send the message signal 24 to the healthcare facility call system 22 in response to the identification signal 36 from the signal processing unit. In the illustrated embodiment, the interface unit 48 comprises a switch 50 that produces a contact closure, similar to when a nurse call button is manually actuated by a patient, when an identification signal is generated. The contact closure produces the message signal that is sent to the healthcare facility call system 22 (FIG. 1), triggering notification of a nurse or other person that an acoustic alarm was identified.

In response to the identification signal 36, the interface unit 48 may also produce a message signal 24 that comprises a series of momentary contact closures of the switch 50. The duration of the contact closure or the time between the start of the contact closures correspond to a unique code recognized or decoded by the healthcare facility call system 22 (FIG. 1). In this way, the type of acoustic alarm 26 may be differentiated by the healthcare facility call system. For example, an infusion acoustic alarm from an infusion pump may result in a message signal having one short and two long contact periods. The healthcare facility call system, upon recognizing this message signal, indicates to the appropriate clinician that an infusion acoustic alarm is sounding. In a further example, a vital sign acoustic alarm from a patient monitoring device may have a different acoustic signature than the infusion acoustic alarm so as to result in different message signal having two short and one long contact periods. The healthcare facility call system, upon recognizing this different message signal, indicates to the appropriate clinician that a vital sign acoustic alarm is sounding. It will be appreciated that other codes, including but not limited to Morse code, may be used to differentiate types of alarms.

Figure 3:
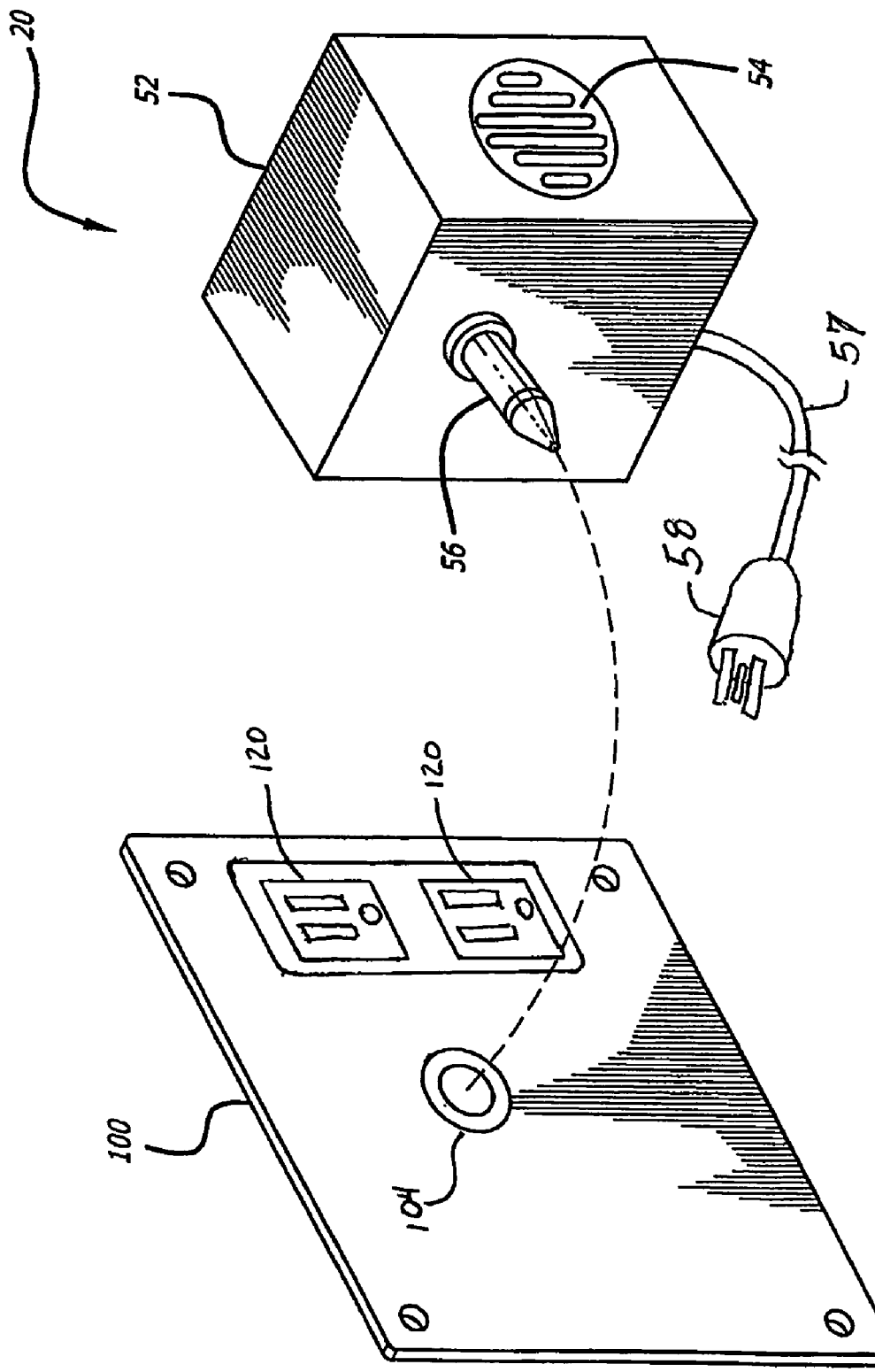
FIG. 3 is a perspective diagram of the nurse call panel similar to that of FIG. 1 at which may be mounted a medical notification apparatus in accordance with aspects of the invention, the medical notification apparatus having a microphone and signal processing equipment with a housing and having a plug for engaging a jack at which the nurse call cable and switch for the patient is usually mounted, the medical notification apparatus also having in this embodiment a power cord and a plug for connection to a main power source at the panel for powering the medical notification apparatus.

In FIG. 3 the medical notification apparatus 20 has a protective cover or housing 52 with openings 54 to allow sound to reach the acoustic sensor 30 inside the housing. The housing also contains the interface unit 48 (FIG. 2), which preferably comprises a communications plug 56 adapted to connect to a cooperatively shaped jack, such as a standard input jack 104 on a nurse call panel 100 on the wall of a patient's room. The communications plug serves as a communications link and as a means of temporarily securing the medical notification apparatus to the preexisting nurse call panel. Also a power cord 57 with a power plug 58 extends from the power source 31 (FIG. 2) inside the housing and is connected to an AC power outlet 120 on the nurse call panel 100. Thus, it will be appreciated that the medication notification apparatus may be rapidly installed in and removed from a patient's room whenever desired. In an alternative embodiment, the medical notification apparatus 20 may be powered alternatively. For example, battery power may be used, or power may be provided through the plug 56, or otherwise. Also, the housing may be mounted to the nurse call panel in other ways, or mounted adjacent the nurse call panel. Also, means may be provided for continuing use of the standard patient's button and cable 108 and 110. The housing 52 may be provided with a jack for receipt of the patient's cable plug 106 and the medical notification apparatus may recognize a patient signal and pass it through. However, other means may also be used.

Figure 4:
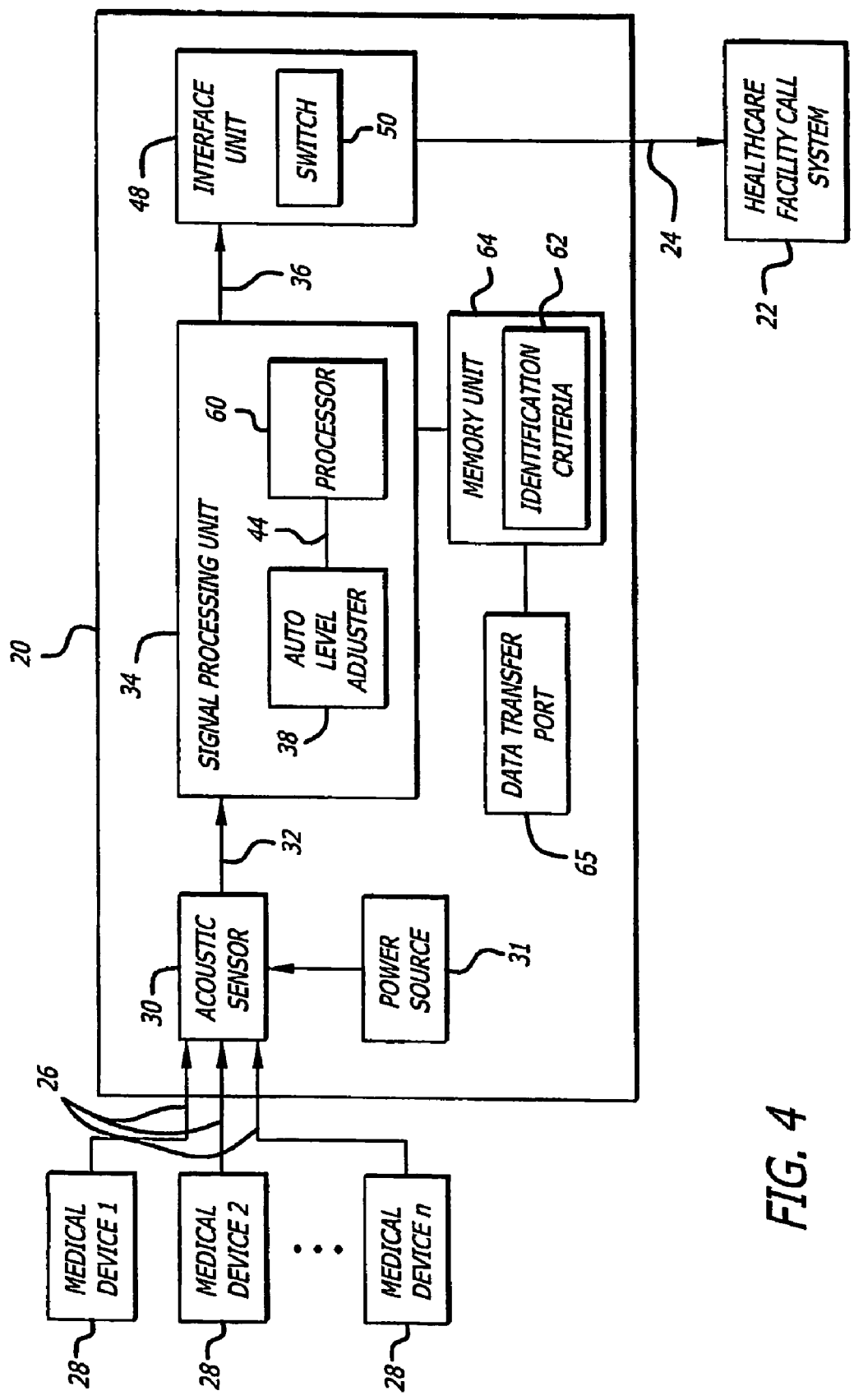
FIG. 4 is a block diagram of a medical notification apparatus in accordance with another embodiment showing an acoustic sensor for sensing an acoustic alarm from a number of medical devices, a signal processing unit comprising an automatic level adjuster and a processor for determining whether the acoustic alarm satisfies an identification criterion stored in a memory unit, a data transfer port for programming, and an interface unit for sending a message signal to a healthcare facility call system.

Referring now to FIG. 4, a signal processing unit 34 in another exemplary embodiment of the present invention comprises an automatic level adjuster 38 and a processor 60. The characteristics of the automatic level adjuster are carefully selected based in part on the output characteristics of the acoustic sensor 30 and the input requirements of the processor. Preferably, the processor is a digital microprocessor and is configured to perform active filtering and to execute a Fast Fourier Transform ("FFT") routine to analyze the conditioned sensor signal 44. The FFT routine comprises determining whether the sensed acoustic alarm 26, represented by the conditioned sensor signal, satisfies an identification criterion or a set of rules 62. The identification criterion 62 may, without limitation, include a predetermined frequency band and a predetermined pulse pattern or rate. When the identification criterion is satisfied, an identification signal 36 is generated by the signal processing unit. In response, a switch 50 in the interface unit 48 produces a contact closure. The contact closure forms a message signal 24 that is sent to the healthcare facility call system 22 (FIG. 1), triggering notification of a nurse or other person that an acoustic alarm was identified in a particular patient's room.

The message signal 24 from the interface unit 48 of FIG. 4 may be a single contact closure. Alternatively, the message signal may be a string or series of momentary contact closures producing a closure pattern that would be decoded by the healthcare facility call system 22, as previously described in connection with FIG. 3.

Still referring to FIG. 4, the processor 60 executes a signal processing program that is stored in an associated memory unit 64 that includes one or more identification criteria 62. The memory unit comprises one or more devices for storing data. Preferably, the memory unit comprises a flash memory device. The memory unit may comprise other forms of Electrically-Erasable Programmable Read-Only Memory (EEPROM) or other types of Non-Volatile Read Write Memory. In any case, the memory unit allows the medical notification apparatus 20 to be rapidly programmed by a technician of the healthcare facility to send a message signal 24 in response to a variety of acoustic alarms 26 from one or more medical devices used by the facility. Also, the medical notification apparatus may be rapidly reprogrammed if necessary whenever a new medical device is introduced. Reprogramming may be performed by uploading new identification criteria to the memory unit via a data transfer port 65 of the medical notification apparatus 20.

Figure 5:
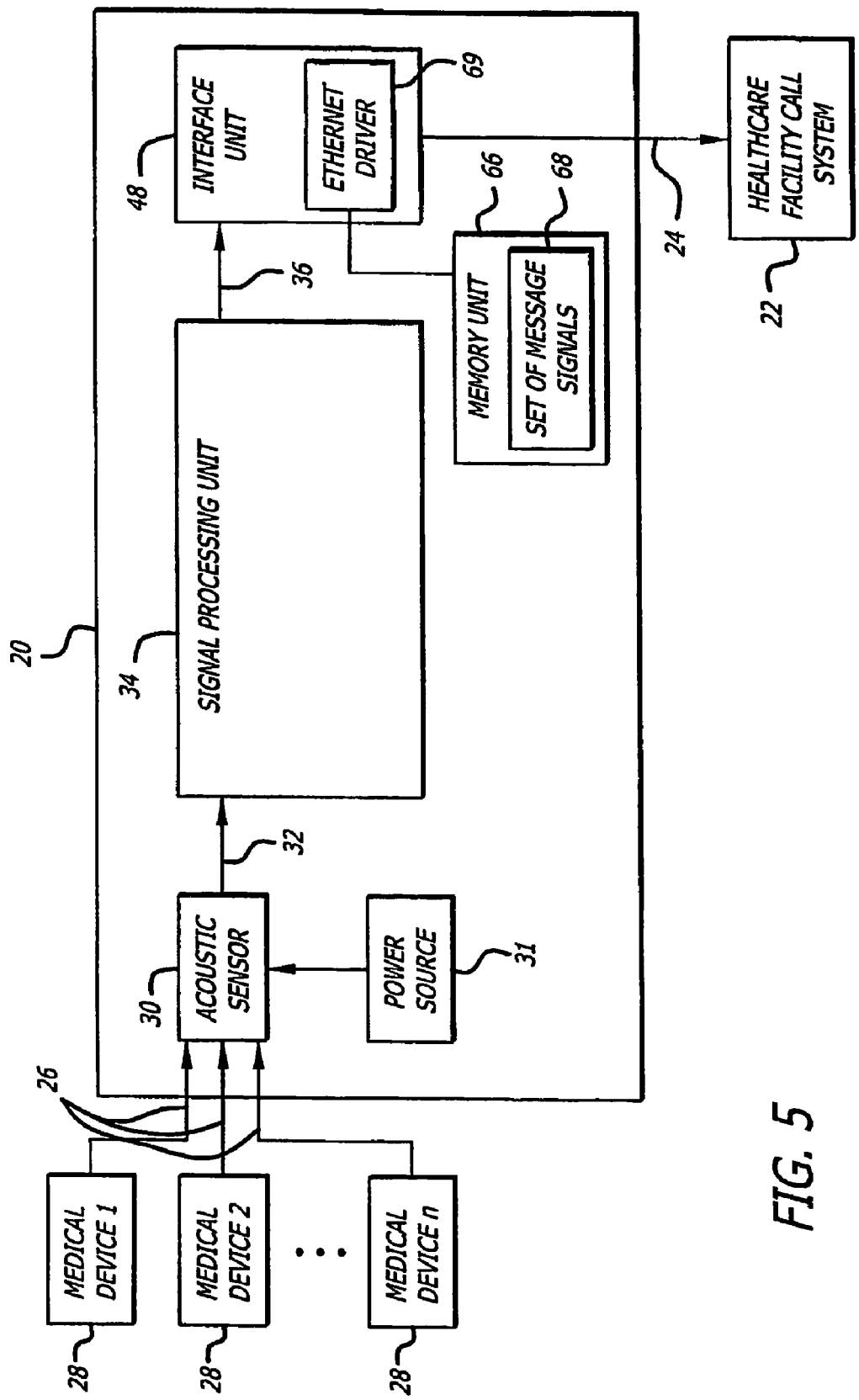
FIG. 5 is a block diagram of a medical notification apparatus in accordance with yet another embodiment showing an acoustic sensor for sensing an acoustic alarm from a number of medical devices, a signal processing unit, an interface unit comprising an Ethernet driver for sending a message signal associated with the sensed acoustic alarm and selected from among a set of message signals stored in a memory unit.

Referring next to FIG. 5, a medical notification apparatus 20 of another embodiment of the present invention is configured to send a different message signal 24 with each type of acoustic alarm 26 identified by the signal processing unit 34. For example, different message signals could be sent to the healthcare facility call system 22 (FIG. 1) in response to a near-end-of-infusion alarm and an occlusion alarm often available from infusion pump devices. Both types of alarms indicate the infusion pump's operational status but require different action from the person being notified. With the appropriate message signal sent to the healthcare facility call system, the person that is notified is able to take the appropriate action without first entering the patient's room to determine the nature of the notification.

A memory unit 66 is associated with the interface unit 48 and is adapted to store a set of message signals 68. This memory unit 66 comprises one or more devices for storing data, which may be shared in common with the memory unit 64 (FIG. 4) associated with the signal processing unit 34. Each one of the set of message signals is associated with a different acoustic alarm. As such, when an acoustic alarm 26 is identified by the signal processing unit 34, the interface unit sends a message signal 24 associated with the identified acoustic alarm from among the stored set of message signals.

With continued reference to FIG. 5, the interface unit 48 of this embodiment comprises an Ethernet driver 69 and communications plug (not shown) adapted to connect to a cooperatively shaped communications port 104, such as an Ethernet port on a nurse call panel 100 on the wall of a patient's room. The Ethernet driver implements an Ethernet communication protocol to send the message signal 24 associated with the identified acoustic alarm 26.

Figure 6:
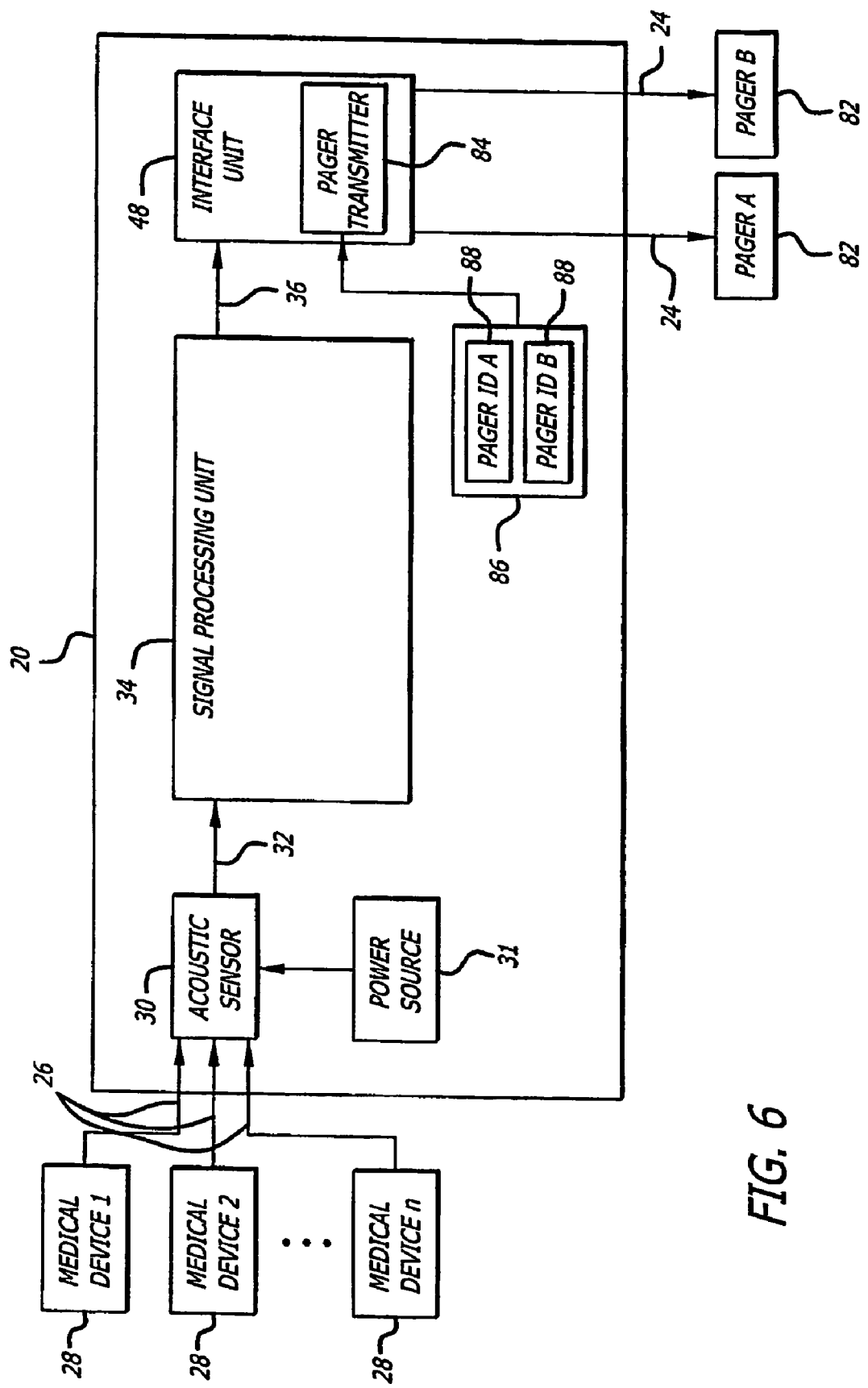
FIG. 6 is a block diagram of another medical notification apparatus showing an acoustic sensor for sensing an acoustic alarm from a number of medical devices, a signal processing unit, an interface unit comprising a pager transmitter for sending a message signal associated with the sensed acoustic alarm to one or more pagers associated with pager identification codes stored in a module of the apparatus.

In FIG. 6 there is shown another exemplary embodiment of a medication notification apparatus 20 that is configured to actuate or send a message to one or more pagers 82 or other portable communication devices carried or worn by healthcare personnel. In this embodiment, the interface unit 48 includes a pager transmitter 84. When the interface unit receives an identification signal 36, it accesses a module 86 containing one or more pager identification codes 88, then transmits a message signal 24 in the form of a radio frequency signal via the pager transmitter to one or more pagers associated with the accessed pager identification codes. Thus, the medication notification apparatus is matched to one or more pagers, which when actuated, produces a vibratory or auditory signal when an acoustic alarm 26 is sensed and identified by the apparatus 20. The pagers may also display an alphanumeric message that may indicate the location of the medication notification apparatus 20. Further, the content of the displayed alphanumeric message may vary depending on the type of acoustic alarm, thereby allowing healthcare personnel that are notified to take appropriate action without first entering the patient's room to determine the nature of the notification.

It will be appreciated that the means of connecting to and communicating with the healthcare facility call system 22 (FIG. 1) is a matter of choice that depends on the requirements of the healthcare facility call system. For example, the medical notification apparatus 20 may be configured to adapt or retrofit to other types of communication networks and protocols, such as 802.11 Wireless Fidelity ("WiFi"). In a case when a healthcare facility call system 22 operates with radio frequency, the interface unit 48 comprises a radio frequency transmitter (not shown) for sending the associated message signal 24 to the healthcare facility call system.

More sophisticated medical devices can be programmed to embed different sonic patterns within an acoustic alarm to further differentiate the alarms. To avoid having a confusing array of different sounding alarms, the embedded sonic patterns may be hidden in the sense that they are outside the normal range of human hearing. The embedded sonic patterns may have a sound wave frequency that is too high (for example, above about 20,000 Hz) or too low (for example, below about 20 Hz) for humans to hear. With embedded sonic patterns, information sent to the health care facility call system 22 can include more than just the type of alarm or medical device that requires attention. For example, there may be two patients in the same room, both patients connected to separate infusion pumps of the same model. Each of the infusion pumps may be adapted to embed different sonic patterns that uniquely identify the pump. As such, when the infusion pump of one patient emits an acoustic alarm, the medical notification apparatus in the two patients' room may send a message, via wireless or wired means, to the healthcare facility call system uniquely identifying the infusion pump requiring attention. When medical devices are uniquely identified with embedded sonic patterns, there is no need for the each of the medical devices to be enabled for radio frequency communication with a wireless hospital information system for the sole purpose of uniquely identifying the pump requiring attention.

Figure 7:
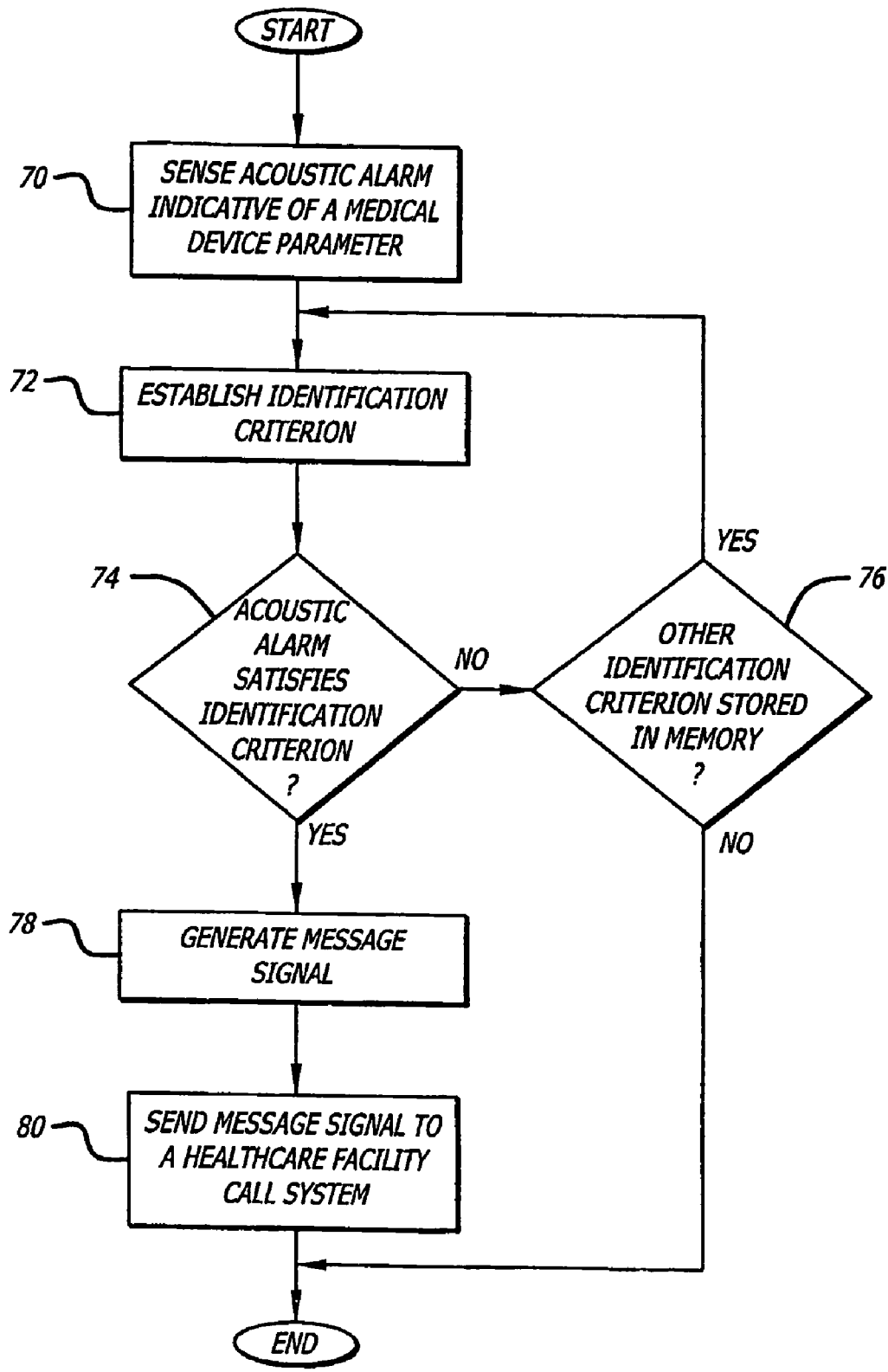
FIG. 7 is a flow diagram of a method in accordance with aspects of the invention for providing a medical notification showing sensing an acoustic alarm and generating a message signal to be sent to a healthcare facility call system when the acoustic alarm satisfies an identification criterion.

There is shown in FIG. 7 a flow diagram of a method of providing medical notification in accordance with the present invention. Although the method will be described in connection with the medical notification apparatus of FIGS. 2-5, it will be appreciated that other medical notification apparatus may be used to implement the method.

Referring to FIG. 7, an acoustic alarm indicative of a medical device parameter is sensed 70. The acoustic alarm may be sensed with a microphone or other type of acoustic sensor. An identification criterion is established 72. The identification criterion may be established by the inherent or selected characteristics of devices, such as a band pass filters and a timing gate, of the signal processing unit. The identification criterion can also be established by accessing a memory unit storing a set of identification criteria.

With continued reference to FIG. 7, a determination 74 is made as to whether the sensed acoustic alarm satisfies the identification criterion. This determination can occur when a sensor signal from an acoustic sensor passes through a band pass filter and a timing gate to produce an identification signal. This determination can performed by a flash programmable processor configured to execute of an FFT routine.

In a case when the sensed acoustic alarm does not satisfy the identification criterion, another identification criterion is established 72 if it is determined 76 that another identification criterion is stored in a memory unit. If no other identification criterion is stored in a memory unit, no further steps are performed.

In a case when the sensed acoustic alarm satisfies the identification criterion, a message signal is generated 78. A message signal may be generated by contact closure of a switch. The message signal can also be generated by selecting a message signal associated with the sensed acoustic alarm from among a set of set of message signals stored in a memory unit. After the message signal is generated, it is sent 80 to a healthcare facility call system.

Thus it will be appreciated that the present invention provides a medication notification system that may be implemented in an existing nurse call system. Medical devices need not be replaced and only one medical notification apparatus is needed in a room having many medical devices. The present invention is also easily implemented in that the medical notification apparatus does not need to be connected with wires to the medical devices and it may be installed rapidly by simply plugging it into a preexisting health facility call system.

While several particular forms of the invention have been illustrated and described, it will also be apparent that various modifications may be made without departing from the scope of the invention. It is also contemplated that various combinations or subcombinations of the specific features and aspects of the disclosed embodiments may be combined with or substituted for one another in order to form varying modes of the invention. Accordingly, it is not intended that the invention be limited, except as by the appended claims.

I claim:

1. A medical notification apparatus comprising:
   an acoustic sensor configured to generate a sensor signal in response to an acoustic alarm that is generated by a medical device and is indicative of a medical device parameter;
   a signal processing unit in communication with the acoustic sensor and configured to generate an identification signal when the sensor signal from the acoustic sensor satisfies an identification criterion; and
   an interface unit in communication with the signal processing unit and configured to send a message signal to a healthcare facility call system in response to the identification signal from the signal processing unit.

2. The apparatus of claim 1 wherein the signal processing unit comprises a signal conditioner having a level adjuster, the signal conditioner adapted to smooth the sensor signal.

3. The apparatus of claim 1 wherein the signal processing unit comprises a band pass filter.

4. The apparatus of claim 1 wherein the signal processing unit comprises a timing gate.

5. The apparatus of claim 1 wherein the signal processing unit comprises an active filter.

6. The apparatus of claim 1 wherein the signal processing unit comprises a processor adapted to execute a fast Fourier transform routine to analyze the sensor signal.

7. The apparatus of claim 1 wherein the identification criterion comprises a frequency band.

8. The apparatus of claim 1 wherein the identification criterion comprises a pulse pattern.

9. The apparatus of claim 1 wherein the interface unit comprises a switch configured to produce a contact closure in response to the identification signal from the signal processing unit.

10. The apparatus of claim 1 wherein the interface unit comprises a radio frequency transmitter configured to transmit a radio frequency signal to the healthcare facility call system in response to the identification signal from the signal processing unit.

11. The apparatus of claim 1 wherein the interface unit comprises a wireless transmitter and is configured to wirelessly transmit a signal to a portable communications device in response to the identification from the signal processing unit.

12. The apparatus of claim 1 wherein the interface unit comprises an Ethernet driver and is configured to transmit an electronic message to the healthcare facility call system in response to the identification signal from the signal processing unit.

13. The apparatus of claim 1 further comprising a memory unit associated with the signal processing unit and storing the identification criterion.

14. The apparatus of claim 1 further comprising a memory unit associated with the interface unit and storing a set of message signals, each one of the set of message signals associated with a different medical device alarm; and wherein the message signal sent to the healthcare facility call system is selected from among the stored set of message signals.

15. A medical notification apparatus for use with a healthcare facility call system, the medical notification apparatus comprising:
 an acoustic sensor configured to generate a sensor signal representative of an acoustic alarm received by the acoustic sensor, the acoustic alarm being generated by a medical device, and is associated with a medical device parameter;
 a signal processing unit connected to the acoustic sensor and configured to store an identification criterion and to determine whether the sensor signal from the acoustic sensor satisfies the stored identification criterion; and
 an interface unit connected to the signal processing unit and configured to send a message signal to the healthcare facility call system when the sensor signal from the acoustic sensor satisfies the stored identification criterion.

16. The apparatus of claim 15 further comprising a memory unit associated with the signal processing unit and the interface unit, the memory unit configured to a store set of identification criteria and a set of message signals, each one of the stored set of message signals associated with one of the stored set of identification criteria; and wherein the message signal sent to the healthcare facility call system is selected from among the stored set of message signals.

17. A method of providing medical notification, the method of comprising:
 sensing an acoustic alarm that is generated by a medical device and is indicative of a medical device parameter; and
 sending a message signal from a medical notification apparatus to a healthcare facility call system in response to the medical notification apparatus identifying the acoustic alarm.

18. The method of claim 17 wherein sending the message from the medical notification apparatus comprises determining whether the acoustic alarm satisfies an identification criterion, and generating the message signal when the acoustic alarm satisfies the identification criterion.

19. The method of claim 17 wherein sending the message from the medical notification apparatus comprises determining whether the acoustic alarm satisfies an identification criterion from among a set of identification criteria, and generating the message signal from among a set of message signals when the acoustic alarm satisfies the identification criterion, each of the set of message signals associated with one of the set of identification criteria.

20. The method of claim 17 further comprising wirelessly transmitting a signal to a portable communications device in response to identifying the alarm.

* * * * *